(12) United States Patent
Passoni et al.

(10) Patent No.: US 10,401,465 B2
(45) Date of Patent: Sep. 3, 2019

(54) COMPENSATION AND CALIBRATION FOR A LOW POWER BIO-IMPEDANCE MEASUREMENT DEVICE

(71) Applicant: STMICROELECTRONICS S.R.L., Agrate Brianza (IT)

(72) Inventors: Marco Passoni, Cornate d'Adda (IT); Alessia Cagidiaco, Pisa (IT); Stefano Rossi, Siena (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 15/380,597

(22) Filed: Dec. 15, 2016

(65) Prior Publication Data

US 2018/0172793 A1     Jun. 21, 2018

(51) Int. Cl.
    *A61B 5/00*         (2006.01)
    *A61B 5/053*       (2006.01)
    *G01R 35/00*      (2006.01)

(52) U.S. Cl.
    CPC ............ *G01R 35/005* (2013.01); *A61B 5/053* (2013.01); *A61B 5/7203* (2013.01);
(Continued)

(58) Field of Classification Search
    CPC ... G01R 35/005; A61B 5/7228; A61B 5/7203; A61B 5/053; A61B 5/7225; A61B 5/7221; A61B 2560/0209; A61B 2560/0223
See application file for complete search history.

(56) References Cited

U.S. PATENT DOCUMENTS

| | | |
|---|---|---|
| 8,909,333 B2 | 12/2014 | Rossi |
| 9,307,924 B2 | 4/2016 | Rossi |

(Continued)

FOREIGN PATENT DOCUMENTS

| | | | |
|---|---|---|---|
| EP | 2767230 A1 | 8/2014 | |
| EP | 2974652 A1 * | 1/2016 | ............. A61B 5/053 |

OTHER PUBLICATIONS

"MEDRC|Analog Devices, Ahead of What's Possible," retrieved Aug. 22, 2016 at http://www.analog.com/en/landing-pages/001/medrc.html, 4 pgs.

(Continued)

*Primary Examiner* — Julian D Huffman
*Assistant Examiner* — Michael T Konczal
(74) *Attorney, Agent, or Firm* — Seed IP Law Group LLP

(57) ABSTRACT

A method and apparatus for compensating and calibrating a bio-impedance measurement device are provided. In the method and apparatus, a memory stores a plurality of compensation parameters and a first detection channel receives a first detection signal, compensates the first detection signal using a first compensation parameter of the plurality of compensation parameters. In the method and apparatus, a second detection channel receives a second detection signal and a third detection signal and compensates the second and third detection signals using second and third compensation parameters of the plurality of compensation parameters and the compensated first detection signal. The impedance measurement device generates a first output signal representative of a first impedance measurement and a second output signal representative of a second impedance measurement based on the compensated first, second and third detection signals.

20 Claims, 8 Drawing Sheets

(52) U.S. Cl.
CPC .......... *A61B 5/7221* (2013.01); *A61B 5/7225* (2013.01); *A61B 5/7228* (2013.01); *A61B 5/7235* (2013.01); *A61B 5/7278* (2013.01); *A61B 5/681* (2013.01); *A61B 5/6804* (2013.01); *A61B 2560/0209* (2013.01); *A61B 2560/0223* (2013.01)

(56) References Cited

U.S. PATENT DOCUMENTS

| | | | |
|---|---|---|---|
| 2008/0001735 A1* | 1/2008 | Tran | G06F 19/3418 340/539.22 |
| 2013/0006136 A1 | 1/2013 | Biancolillo et al. | |
| 2014/0094675 A1* | 4/2014 | Luna | A61B 5/02438 600/386 |
| 2014/0308930 A1* | 10/2014 | Tran | H04W 4/001 455/414.1 |
| 2015/0051505 A1 | 2/2015 | Rossi | |

OTHER PUBLICATIONS

Rossi, S. et al., "A low power bioimpedance module for wearable systems," *Sensors and Actuators A* 232:359-367, 2015.

\* cited by examiner

COMPENSATION AND CALIBRATION FOR A LOW POWER BIO-IMPEDANCE MEASUREMENT DEVICE

BACKGROUND

Technical Field

This application is directed to a bio-impedance measurement device that is calibrated to compensate the inaccuracies of the impedance measurements.

Description of the Related Art

Bio-impedance measurement has a wide range of applications. Bio-impedance may be used to determine the composition of a biological body. Bio-impedance may also be used to determine the cardiac output of the biological body and its breathing rate. An accurate bio-impedance measurement aids in accurately characterizing the conditions of the biological body. However, conventional bio-impedance measurement devices introduce errors that result in inaccurate bio-impedance measurements.

Wearable and portable devices have low power consumption requirements, such as the architectures described in U.S. Pat. Nos. 8,909,333 and 9,307,924 and U.S. Patent Application Publication Nos. 2013/0006136 and 2015/0051505. However, when working frequency is increased, the accuracy of these solutions is degraded. Therefore, for a multi-frequency (or high single frequency) device, novel architectural solutions are needed to enable high accuracy with low power consumption. It is desirable to compensate for the errors and inaccuracies introduced in the bio-impedance measurements made by a bio-impedance measurement device.

BRIEF SUMMARY

In an embodiment, an impedance measurement device includes memory configured to store a plurality of compensation parameters and a first detection channel configured to receive a first detection signal and compensate the first detection signal using a first compensation parameter of the plurality of compensation parameters. The impedance measurement device also includes a second detection channel configured to receive a second detection signal and a third detection signal and compensate the second and third detection signals using second and third compensation parameters of the plurality of compensation parameters and the compensated first detection signal. The impedance measurement device generates a first output signal representative of a first impedance measurement and a second output signal representative of a second impedance measurement based on the compensated first, second and third detection signals.

In an embodiment, the first and second detection channels are configured to compensate for a relative time quantization error introduced in a trigger signal used for sampling the first detection signal and the second and third detection signals. In an embodiment, compensating the first detection signal using the first compensation parameter includes scaling an amplitude and adjusting a phase of the first detection signal by the first compensation parameter. In an embodiment, the first compensation parameter is a complex value. In an embodiment, generating the first output signal includes demodulating the compensated first detection signal to produce a first demodulated signal, filtering the first demodulated signal and compensating the filtered first demodulated signal to produce the first output signal.

In an embodiment, compensating the second and the third detection signals using the second and the third compensation parameters includes determining a difference between the second and the third detection signals, compensating the difference between the second and the third detection signals by the second compensation parameter, determining a common mode voltage based on the compensated difference between the second and the third detection signals and the compensated first detection signal, compensating the common mode voltage by the third compensation parameter and reducing the scaled difference between the second and the third detection signals by the scaled common mode voltage.

In an embodiment, generating the second output signal includes demodulating the second and third detection signals, amplifying the difference between the second and the third detection signals to produce an amplified signal, filtering the amplified signal and compensating the filtered amplified signal to produce the second output signal. In an embodiment, the first detection channel includes a first demodulator and the first compensation parameter compensates for a gain of the first demodulator and an absolute time quantization error of the first demodulator.

In an embodiment, the second detection channel includes a second demodulator, a third demodulator and an amplifier and the second compensation parameter compensates for a gain of the second demodulator or the third demodulator and an absolute time quantization error of the second demodulator or the third demodulator and a gain of the amplifier. In an embodiment, the second detection channel is configured to use the third compensation parameter to compensate for a common mode rejection ratio of the second demodulator and the third demodulator.

In an embodiment, a method for calibrating an impedance measurement device includes setting a contact impedance of a plurality of probes of the impedance measurement device to a first impedance value and an impedance between two probes of the plurality of probes to a zero impedance value. In an embodiment, the method includes determining a first detection signal at an input of a first detection channel of the impedance measurement device and a first output signal at an output of the first detection channel. In an embodiment, the method includes determining a first compensation parameter based on the first detection signal and the first output signal. In an embodiment, the method includes detecting a second and a third detection signals at respective first and second inputs of a second detection channel of the impedance measurement device and a second output signal at an output of the second detection channel.

In an embodiment, the method includes compensating, in the first and second detection channels, for a relative time quantization error introduced in a trigger signal used for sampling the first, second and third detection signals. In an embodiment, the method includes setting a contact impedance of a plurality of probes of the impedance measurement device to a zero impedance value and an impedance between two probes of the plurality of probes to a second impedance value. In an embodiment, the method includes determining fourth and fifth detection signals at the respective first and second inputs of the second detection channel and a third output signal at the output of the second detection channel. In an embodiment, the method includes determining second and third compensation parameters based on the second, third, fourth and fifth detection signals and the second and third output signals. In an embodiment, the method includes causing the first, second and third compensation parameters to be stored in the impedance measurement device for compensating an impedance measurement to be made by the impedance measurement device.

In an embodiment, the method includes receiving a first detection signal, compensating the first detection signal using a first compensation parameter of the plurality of compensation parameters, receiving a second detection signal and a third detection signal, compensating the second and third detection signals using second and third compensation parameters of the plurality of compensation parameters and the compensated first detection signal and generating a first output signal representative of a first impedance measurement and a second output signal representative of a second impedance measurement based on the compensated first, second and third detection signals.

DETAILED DESCRIPTION

Figure 1:
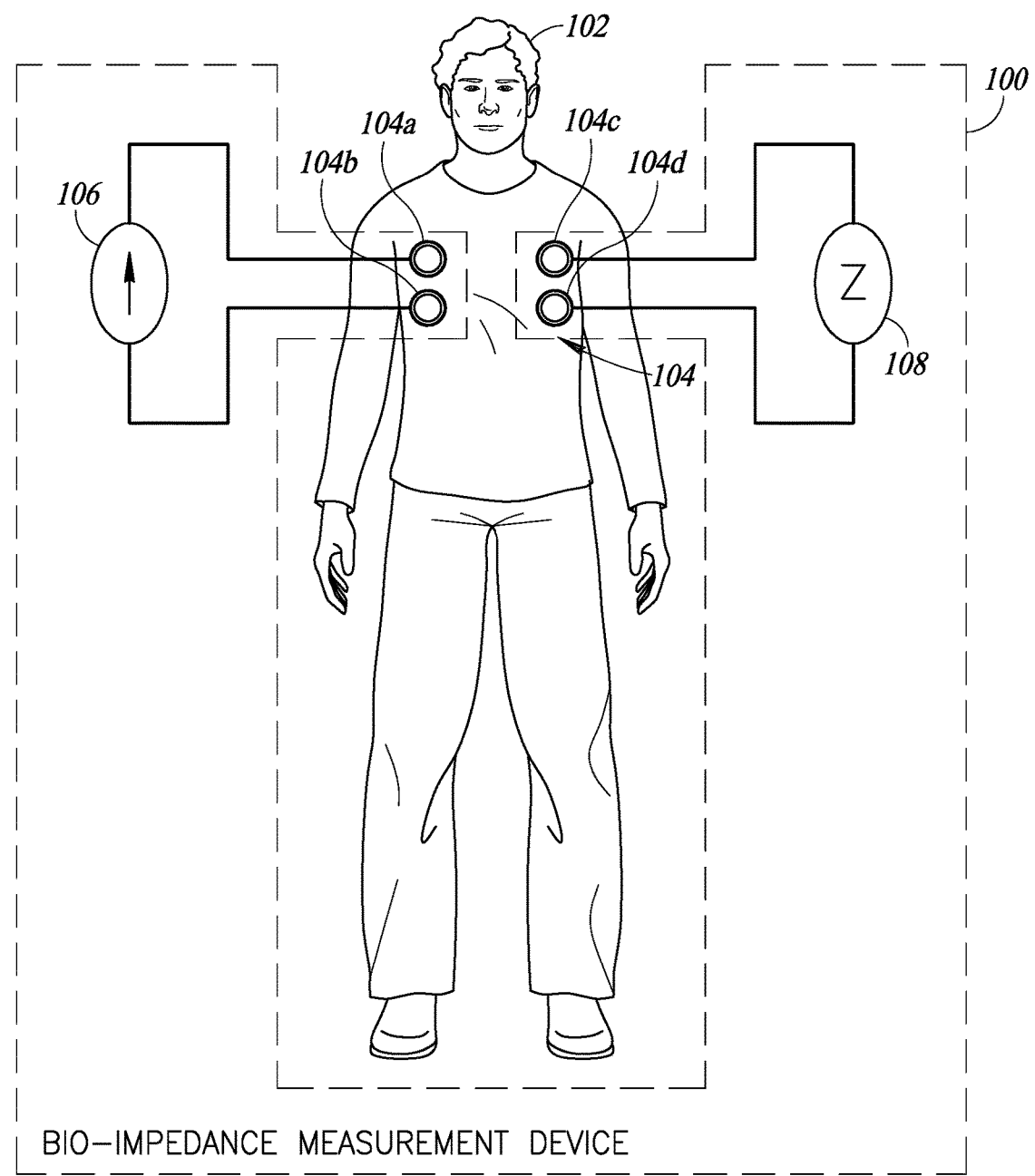
FIG. 1 shows a bio-impedance measurement device in contact with a biological body.

FIG. 1 shows a bio-impedance measurement device 100 in contact with a biological body 102. The bio-impedance measurement device 100, referred to hereinafter as the measurement device 100, includes a plurality of electrodes 104a-104d (collectively referred to herein as electrodes 104), a current generator 106 and a voltage detector 108. The current generator 106 is coupled to a first electrode 104a and a second electrode 104b of the plurality of electrodes 104. The voltage detector 108 is coupled to a third electrode 104c and a fourth electrode 104d of the plurality of electrodes 104.

The plurality of electrodes 104 make contact with the biological body 102. For example, each electrode 104 may be positioned to be in contact with the skin or tissue of the biological body 102. The measurement device 100 may be any device that measures the impedance (also known as the bio-impedance or bioelectrical impedance) of an object. Impedance is a measure of the opposition to current by the object. The impedance of the biological body 102 may be indicative of the composition of the biological body 102. For example, the impedance of the biological body 102 may be used to determine an amount of water or liquids in the biological body, fat-free body mass, or body fat.

The current generator 106 supplies current between the first and second electrodes 104a, 104b. The voltage detector 108 measures the impedance across the third and fourth electrodes 104c, 104d. Measuring the impedance may be based on a voltage detected at the third and fourth electrodes 104c, 104d. As described herein, the measurement device 100 may also measure the impedance at the first and second electrodes 104a, 104b and utilize the measurement to improve impedance detection.

The measurement device 100 may be a wearable device. For example, the measurement device 100 may be part of a watch, an activity tracker, an armband, a chest band or a patch, among others. The measurement device 100 may be used to provide biometrics, for example, to a user. The biometrics may include body composition or fluid content among others.

Figure 2:
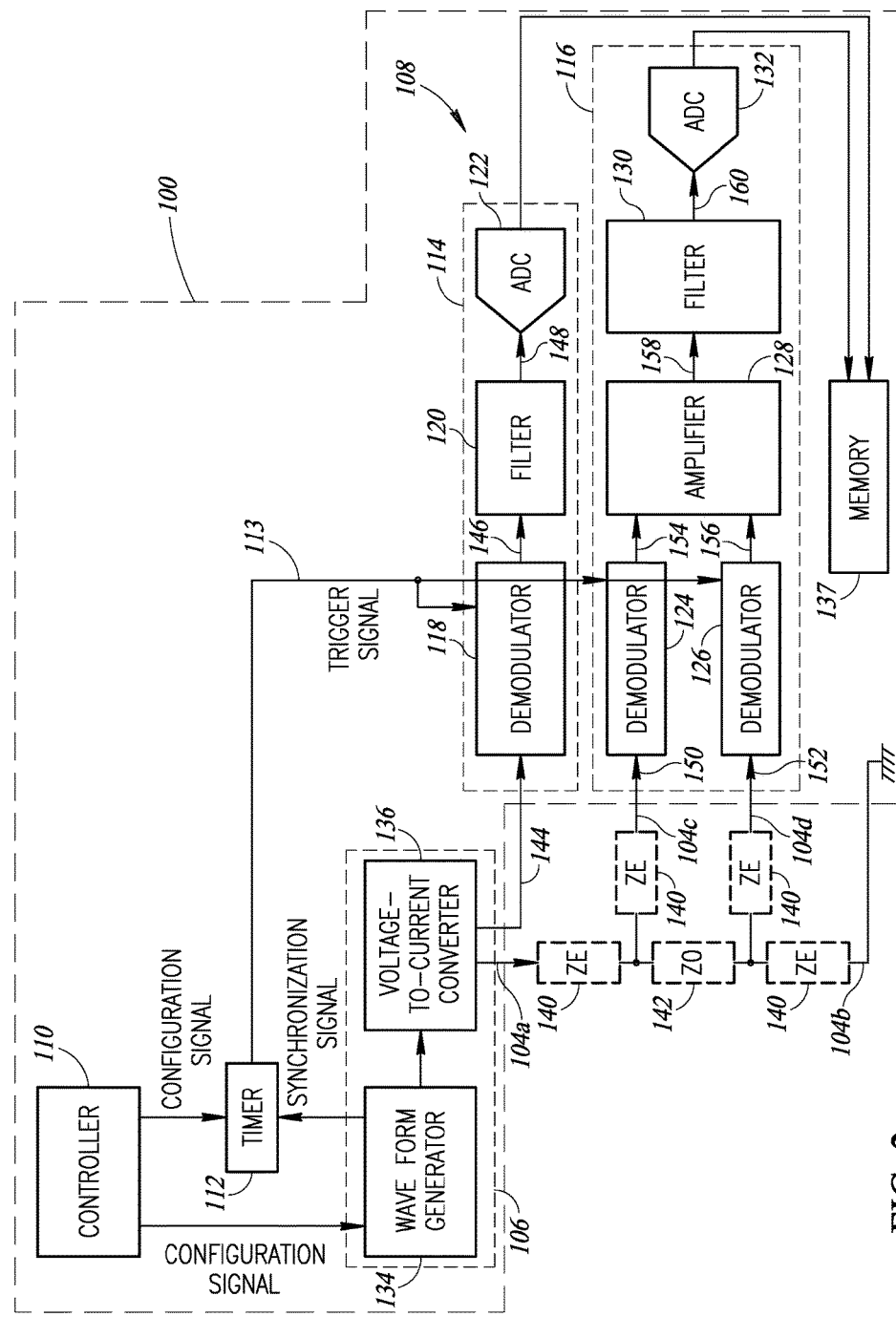
FIG. 2 shows a block diagram of the measurement device.

FIG. 2 shows a block diagram of the measurement device 100. The measurement device 100 includes the plurality of electrodes 104, the current generator 106, the voltage detector 108, a controller 110 and a timer 112. The voltage detector 108 includes a first detection channel 114 and a second detection channel 116. The first detection channel 114 includes a first demodulator 118, a first filter 120 and a first analog-to-digital converter (ADC) 122. The second detection channel 116 includes a second demodulator 124, a third demodulator 126, and amplifier 128, a second filter 130 and a second ADC 132. The first and second filters 120, 130 may be low-pass filters. The current generator includes a waveform generator 134 and a voltage-to-current converter 136. The measurement device 100 also includes memory 137. It is noted that in an embodiment, the first and second ADCs 122, 132 may be integrated into the controller 110. Furthermore, the controller 110 may perform the functions of the first and second ADCs 122, 132.

The measurement device 100 reduces power consumption. In particular the use of the demodulators before the amplification in the channels 116, 114 enables the use of a narrower bandwidth amplifier. Thus reduces both power consumption and device cost. Furthermore, the detection channel 114 may use a voltage output of the voltage-to-current converter 136 to measure the impedance of the body (Z0) plus the electrode-to-skin contact impedances.

The controller 110 sets the frequency for operating waveform generator 134 and the demodulators 118, 124, 126. The controller 110 outputs a configuration signal indicating the frequency. The waveform generator 134 receives the configuration signal and generates a waveform having the frequency. The waveform may, for example, be a sine waveform among others. The waveform generator 134 outputs the waveform to the voltage-to-current converter 136.

The waveform generator 134 outputs a synchronization signal to the timer 112. The timer 112 receives the synchronization signal from the waveform generator 134 and also receives the configuration signal from the controller 110. The timer 112 outputs a trigger signal 113 to the demodulators 118, 124, 126. The demodulators 118, 124, 126 synchronously sample the detected voltage, based on the trigger signal, generating voltage signals proportional to the real and imaginary parts of the impedances.

The voltage-to-current converter 136 receives the waveform from the waveform generator 134. The voltage-to-current converter 136 converts the waveform from a voltage signal to a current signal. The voltage-to-current converter 136 outputs of the current signal over the first electrode 104a. The second electrode 104b may be connected to the ground. The current is supplied to the biological body 102 between the first and second electrodes 104a, 104b.

The first detection channel 114 has an input coupled to the first electrode 104a. The input may be a voltage signal generated by the voltage-to-current converter 136. The voltage signal may be proportional to the voltage drop between the electrodes 104a, 104b. The input signal is described in U.S. Pat. No. 8,909,333. The second detection channel 116 has a first input coupled to the third electrode 104c and a second input coupled to the fourth electrode 104d. The first detection channel 114 operates on an input received from the first electrode 104a and produces a first filtered signal 148 ($V_{INJ,3}$). The second detection channel 116 operates on inputs received at the third and fourth electrodes 104c, 104d. The second detection channel 116 produces a second filtered signal 160 ($V_{O,4}$). The first filtered signal 148 and the second filtered signal 160 are then used to determine a measurement of a contact impedance ($Z_E$) (denoted as contact impedance 140) and a measurement of the bio-impedance ($Z_O$) (denoted as bio-impedance 142) of the biological body 102 as described herein. The contact impedance 140 is the impedance made between one of the electrodes 104 and the biological body 102.

In particular, the first demodulator 118 receives a first detection signal 144 that is output from the first electrode 104a. The first demodulator 118 demodulates the first detection signal 114 based on the trigger signal 113 and outputs a first demodulated signal 146. The first demodulated signal 146 is provided to the first filter 120. The first filter 120 receives the first demodulated signal 146 and filters the demodulated signal 146. The first filter 120 may low-pass filter the first demodulated signal 146. The first filter 120 outputs a first filtered signal 148. The first filtered signal 148 may be converted from analog to digital format by the first analog-to-digital converter 122.

In the second detection channel 116, the second demodulator 124 receives a second detection signal 150 that is output from the third electrode 104c. The third demodulator 126 receives a third detection signal 152 that is output from the fourth electrode 104d. The second demodulator 124 demodulates the second detection signal 150 based on a timing of the trigger signal 113. The second demodulator 124 outputs a second demodulated signal 154. The third demodulator 126 demodulates the third detection signal 152 based on a timing of the trigger signal 113. The third demodulator 126 outputs a third demodulated signal 156.

The amplifier 128 receives the second and third demodulated signals 154, 156. The amplifier 128 compares the second and third demodulated signals 154, 156. The amplifier 128 outputs an amplified signal 158 based on a difference between the third demodulated signal 156 and the second demodulated signal 154. The second filter 130 receives the amplified signal 158. The second filter 130 filters the amplified signal 158 to produce the second filtered signal 160. The second filter 130 may be a low-pass filter and may remove, from the amplified signal 158, frequency components that are higher than a threshold frequency. The second filtered signal 160 may be converted from analog format to digital format by the second analog-to-digital converter 132.

The first filtered signal 148 and the second filtered signal 160 may then be used to determine the detected contact impedance 140 and the detected bio-impedance 142 as described herein.

The memory 137 is configured to store compensation parameters. The compensation parameters are used to compensate the output signals of the first and second ADCs 122, 132.

The accuracy of measuring the bio-impedance 142 by the measurement device 100 is affected by several factors. The factors include an input parasitic impedance, e.g. a parasitic capacitance, to the demodulators and a gain accuracy of the demodulators 118, 124, 126. The factors also include a common mode rejection ratio of the second and third demodulators 124, 126. The factors affecting accuracy of the bio-impedance 142 measurement include the clock granularity of the trigger signal 113 and a delay associated with many blocks of the circuit, e.g. the trigger signal 113 the demodulators 118, 124, 126, the voltage-to-current converter 136, etc. Further, the accuracy of the waveform generator 134 also influences the accuracy of measuring the bio-impedance 142. These error sources become especially critical when the power consumption is reduced. Low power consumption, i.e., requires the use of limited clock speed and of components with bandwidth as narrow as possible. Therefore, limited performances, like reduced CMRR, not negligible parasitic, lower clock granularity shall be expected, especially for high working frequency of the system.

As described herein, the measurement device 100 is calibrated to compensate for the factors that introduce inaccuracies in the bio-impedance measurement. After the measurement device is calibrated, the accuracy of the bio-impedance measurement is improved. The measurement device 100 may be calibrated during or after manufacture. The measurement device 100 may be configured to compensate for the sources of inaccuracy. When the measurement device 100 is used, the accuracy of bio-impedance measurement is improved as a result of the calibration and compensation of the sources of inaccuracy.

The measurement device 100 may be calibrated by applying a known contact impedance 140 and a known bio-impedance 142. For example, the measurement device may be used to measure the known impedances 140, 142. Thereafter, a plurality of compensation parameters may be obtained. The measurement device 100 may then be configured to compensate for the plurality of measured compensation parameters. Calibration may be performed during or after manufacture of the measurement device 100. Parameter compensation may be performed while the measurement device 100 is being used, for example, by a user.

Figure 3:
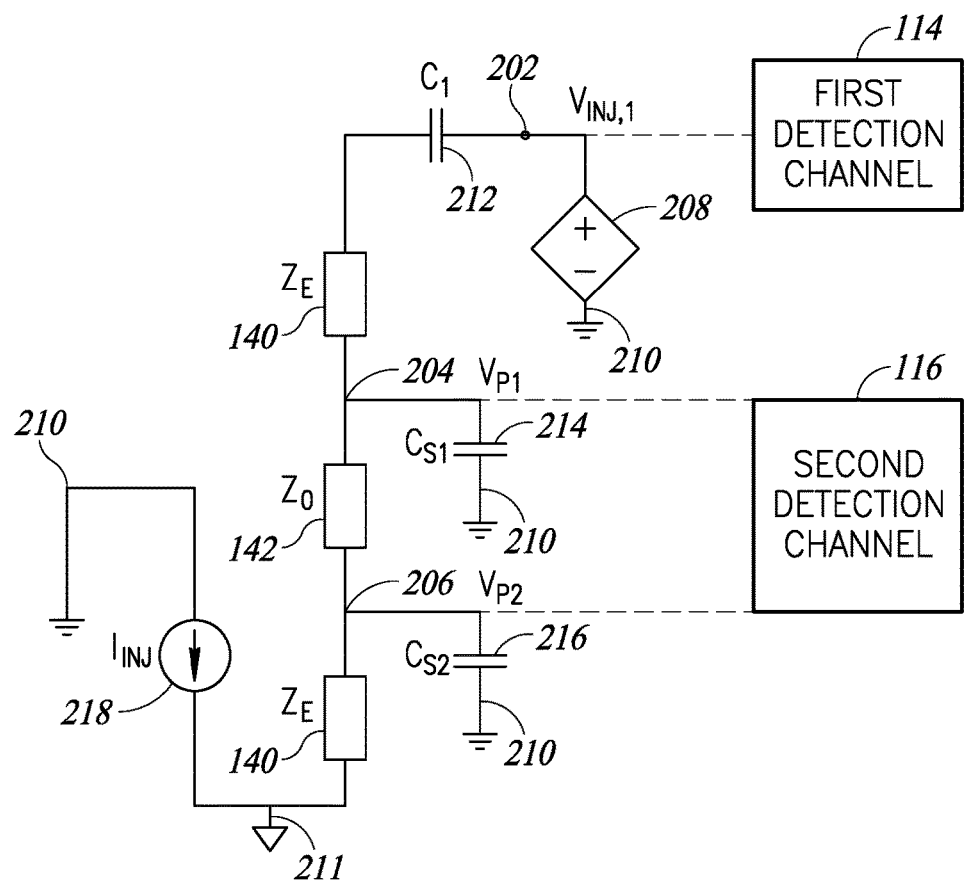
FIG. 3 shows a schematic of a circuit that models capacitances at an input of the first and second detection channels of the measurement device.

FIG. 3 shows a schematic of a circuit that models capacitances at inputs of the first and second detection channels 114, 116 of the measurement device 100. The first detection channel 114 receives an injected voltage ($V_{INJ,1}$). The second detection channel 116 receives a first voltage ($V_{P1}$) and a second voltage ($V_{P2}$). The injected voltage is a voltage of a voltage injection node 202. The first and second voltages are voltages of a first node 204 and a second node 206, respectively.

A voltage source 208 has a cathode coupled to the voltage injection node 202 and an anode coupled to a ground node 210. A first impedance, e.g. a capacitance 212 (denoted as $C_1$) may be coupled in series to the contact impedance 140 for safety reasons, preventing DC current to flow in the body. The first capacitance 212 and the contact impedance 140 are together coupled between the voltage injection node 202 and the first node 204.

A second impedance, e.g. a second parasitic capacitance 214 (denoted as $C_{s1}$) is coupled between the first node 204 and the ground node 210. The bio-impedance 142 is coupled between the first and second nodes 204, 206. A third impedance, e.g. a third parasitic capacitance 216 (denoted as $C_{s2}$) is coupled between the second node 206 and the ground node 210. The value of $C_{s1}$ and $C_{s2}$ may be determined, e.g., through datasheet of components, simulations or measurements. Another contact impedance 140 is coupled between the second node 206 and the ground node 210. A current source 218 that provides an injected current ($I_{INJ}$) has an anode coupled to the contact impedance 140 and a cathode coupled to a virtual ground node 211. The virtual ground node 211 may be a node that is kept to the same voltage as a ground node, but current cannot flow into the virtual ground node 211

The current generated by the current source 218 is partially absorbed by the capacitances 212, 214, 216. Due to the capacitances 212, 214, 216, the injection voltage ($V_{INJ,1}$) received by the first detection channel 114 and the first voltage ($V_{P1}$) and the second voltage ($V_{P2}$) received by the second detection channel 116 are changed.

The injection voltage is a function of the bio-impedance 142, contact impedance 140, first, second and third capacitances 212, 214, 216 and injection current. The injection voltage may, therefore, be represented as:

$$V_{INJ,1}=f_1(Z_0,Z_E,C_{s1},C_{s2},C_1,I_{INJ}). \quad \text{Equation (1)}$$

Similarly, the first voltage and the second voltage are functions of the bio-impedance 142, contact impedance 140, first, second and third capacitances 212, 214, 216 and injection current. In addition, the difference between the first voltage and the second voltage is a function of the quantities and may be represented as:

$$V_{d,1}=V_{P1}-V_{P2}=f_2(Z_0,Z_E,C_{s1},C_{s2},C_1,I_{INJ}). \quad \text{Equation (2)}$$

The common mode voltage, which is the average of the first and second voltages, may be represented as:

$$V_{CM} = \frac{V_{P1}+V_{P2}}{2} = f_3(Z_0, Z_E, C_{s1}, C_{s2}, C_1, I_{INJ}). \quad \text{Equation (3)}$$

The bio-impedance 142 is function of the injection voltage 208, the difference between the first voltage 204 and the second voltage 206, the first, second and third capacitances 212, 214, 214 and injection current:

$$Z_0=f_4(V_{d,1},V_{INJ,1},C_{s1},C_{s2},C_7,I_{INJ}). \quad \text{Equation (4a)}$$

The contact impedance 140 is function of the injection voltage 208 the difference between the first voltage 204 and the second voltage 206, the first, second and third capacitances 212, 214, 216 and injection current:

$$Z_E=f_5(V_{d,1},V_{INJ,1},C_{s1},C_{s2},C_7,I_{INJ}). \quad \text{Equation (4b)}$$

Similarly, also the common mode voltage can be represented as a function of the injection voltage 208, the difference between the first voltage 204 and the second voltage 206, the first, second and third capacitances 212, 214, 216 and injection current:

$$V_{CM}=f_6(V_{d,1},V_{INJ,1},C_{s1},C_{s2},C_7,I_{INJ}). \quad \text{Equation (4c)}$$

Any skilled person can compute the expression of $f_1$, $f_2$, $f_3$, $f_4$, $f_5$ and $f_6$ from the analysis of the circuit in FIG. 3.

Referring back to FIG. 2, the first detection signal 144 (denoted as $V_{INJ,1}$) received by the first demodulator 118 is the same as the injection voltage. The first demodulated signal 146 that is output by the first demodulator may be represented as:

$$V_{INJ,2}=G_{D,I}V_{INJ,1}e^{jT_{D,I}}, \quad \text{Equation (4d)}$$

where $G_{D,I}$ represents the gain of the first demodulator 118, $T_{D,I}$ represents a first time delay and j represents the unit imaginary number.

The first filtered signal 148 may also be represented as:

$$V_{INJ,3} = V_{INJ,2} \quad \text{Equation (5)}$$
$$V_{INJ,3} = (G_{D,I}e^{jT_{D,I}})V_{INJ,1}$$
$$V_{INJ,3} \stackrel{def}{=} \frac{1}{A_E}V_{INJ,1},$$

where $A_E$ is a compensation parameter associated with the first detection channel 114. It is noted that $V_{INJ,3}=V_{INJ,2}$ is true in the passband of the filter 120.

In the second detection channel 116, the difference between the second detection signal 150 and the third detection signal 152 is given by Equation (2). As described herein, the second and third demodulators 124, 126 respectively demodulate the second and third detection signals 150, 152 and output the second and third demodulated signals 154, 156. The difference between the second and third demodulated signals 154, 156 is denoted herein as $V_{d,2}$ and may be represented as:

$$V_{d,2}=G_{D,0}(V_{d,1}+CMRR_{FD}V_{CM})e^{jT_{D,0}}, \quad \text{Equation (6)}$$

where $G_{D,0}$ represents the gain of the second and third demodulators 124, 126, $CMRR_{FD}$ is the common mode rejection ratio of the of the second and third demodulators 124, 126, $V_{CM}$ is the common mode voltage described with reference to Equation (3) and $T_{D,0}$ is a second time delay.

The amplified signal 158 output by the amplifier 128 may be represented as:

$$V_{0,3}=G_A V_{d,2} \; V_{0,3}=G_A G_{D,0}(V_{d,1}+CMRR_{FD}V_{CM})e^{jT_{D,0}}, \quad \text{Equation (7)}$$

where $G_A$ is the gain of the amplifier 158.

The second filtered signal 160 ($V_{0,4}$) output by the second filter 130 may be assumed to be the same as the amplified signal 158. That is, $V_{0,4}$ may be set to $V_{0,3}$. The second filtered signal 160 may be represented as:

$$V_{0,4}=G_A G_{D,0}(V_{d,1}+CMRR_{FD}V_{CM})e^{jT_{D,0}} \; V_{0,4}=(V_{d,1}+CMRR_{FD}V_{CM})(G_A G_{D,0}e^{jT_{D,0}}). \quad \text{Equation (8)}$$

The second part of Equation (8) may be defined to be a first compensation parameter of the second detection channel 116. The first compensation parameter may be defined as:

$$\frac{1}{A_0} \stackrel{def}{=} (G_A G_{D,0}e^{jT_{D,0}}). \quad \text{Equation (9)}$$

The common mode rejection ratio ($CMRR_{FD}$) may be defined as a second compensation parameter of the second detection channel 116. Thus, the second filtered signal output by the second filter 130 may be represented as $$V_{0,4} = \frac{1}{A_0}(V_{d,1} + CMRR_{FD}V_{CM}). \quad \text{Equation (10)}$$

Figure 4A:
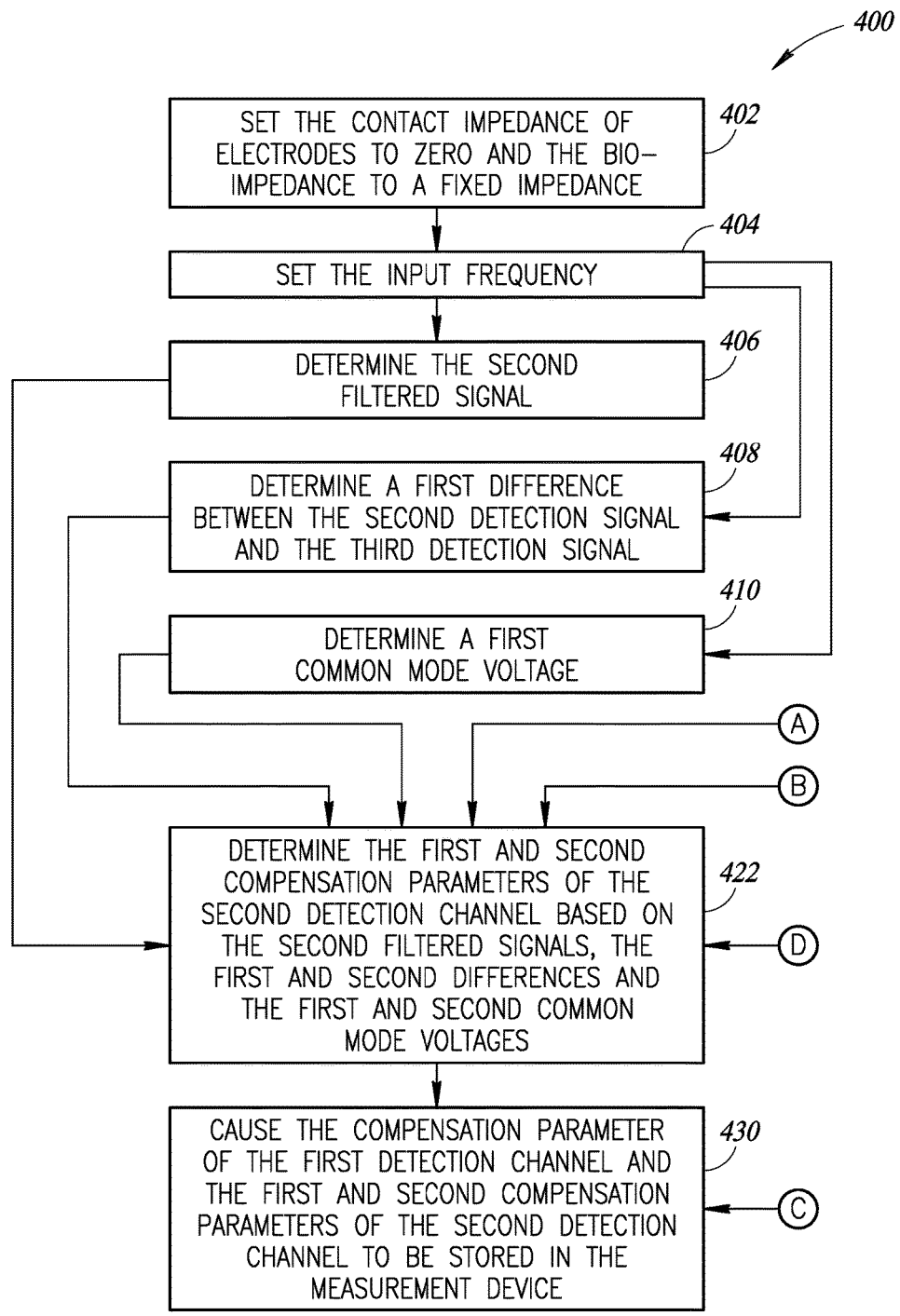
FIGS. 4A and 4B show a block diagram of a method for determining the compensation parameters of the measurement device.
Figure 4B:
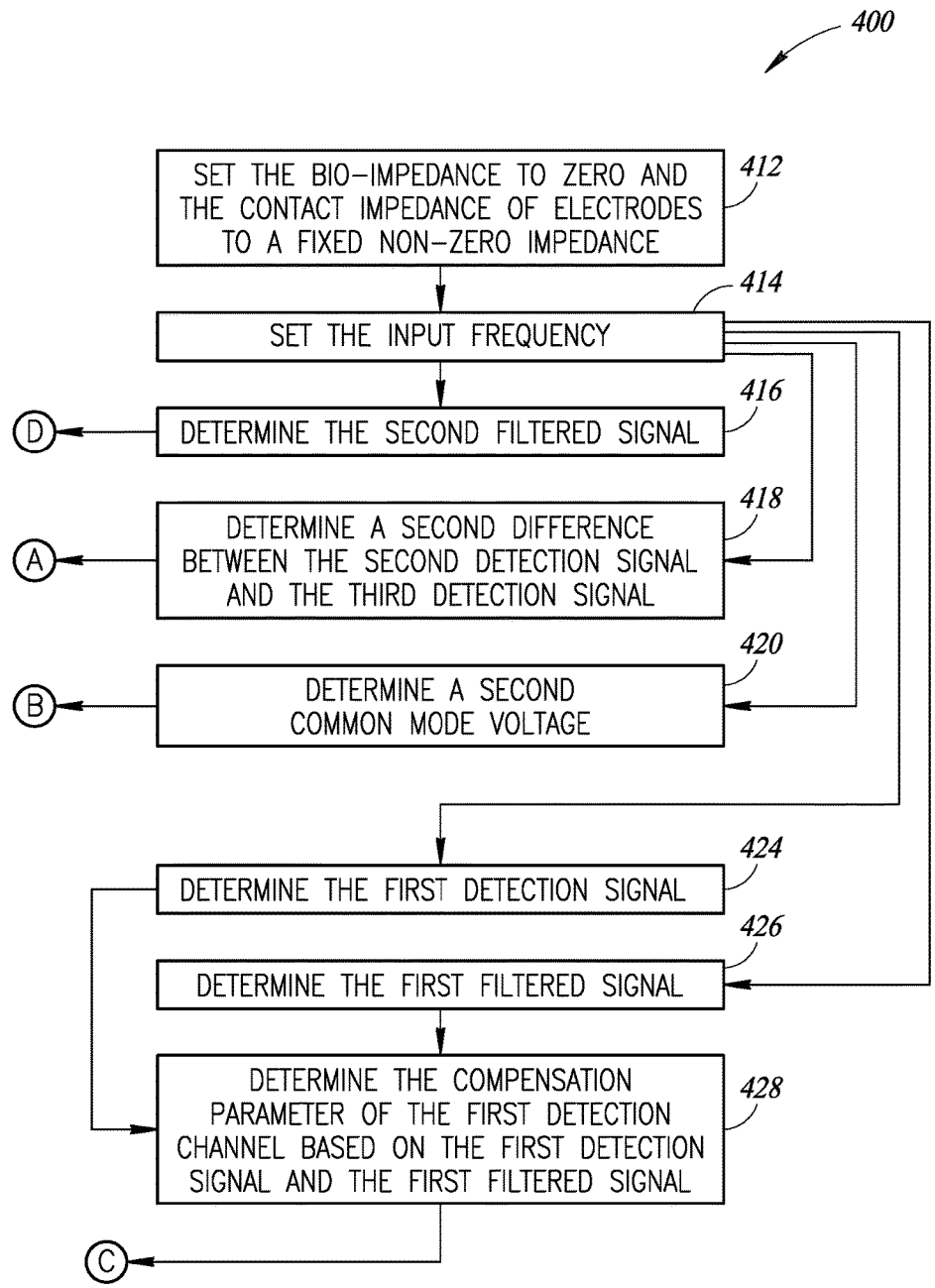

FIGS. 4A and 4B show a block diagram of a method 400 for determining the compensation parameters of the measurement device 100. The method 400 may be performed by a calibration device connected to the measurement device 100. At step 402, the calibration device sets the contact impedance 140 is to zero Ω and the bio-impedance to a fixed impedance. At step 404, the calibration device sets the input frequency of the injection current at a frequency value. At step 406, the calibration device determines second filtered signal 160 (denoted as $\hat{V}_{dm1}$). The second filtered signal 160 is provided at the output of the second filter 130. To determine the second filtered signal, the calibration device may be connected to an output of the second filter 130.

At step 408, the calibration device determines a first difference between the second detection signal 150 and the third detection signal 152, for example using the Equation (2). The first difference is denoted herein as $\hat{V}_{dt1}$. The calibration device calculates the second and third detection signals 150, 152 (and their difference) using Equation (2). That is because the capacitances and the current are known, while the Z0 and ZE are used for the calibration.

The calibration device then determines a first common mode voltage at step 410 (denoted herein as $\hat{V}_{CM1}$). The calibration device may determine the first common mode voltage, for example, using Equation (3).

The method 400 proceeds to step 412. At step 412, the calibration device sets the bio-impedance 142 to zero Ω and the contact impedance 140 of electrodes 104 to a fixed impedance. At step 414, the calibration device sets the input frequency of the injection current at a frequency value. At step 416, the calibration device determines the second filtered signal 160 detected at zero Ω bio-impedance and a fixed contact impedance 140. The second filtered signal 160 is denoted herein as $\hat{V}_{dm2}$. At step 418, the calibration device determines a second difference between the second detection signal 150 and the third detection signal 152 detected at zero Ω bio-impedance and a fixed contact impedance 140. The second difference between the second detection signal 150 and the third detection signal 152 is denoted herein as $\hat{V}_{dt2}$. The calibration device then determines a second common mode voltage (denoted as $\hat{V}_{CM2}$) at step 420.

At step 422, the calibration devices uses the second filtered signal 160 ($\hat{V}_{dm1}$), the first difference signal ($\hat{V}_{dt1}$) and the first common mode voltage ($\hat{V}_{CM1}$) determined at the zero contact impedance and fixed bio-impedance as well as the second filtered signal 160 ($\hat{V}_{dm2}$), the second difference signal ($\hat{V}_{dt2}$) and the second common mode voltage ($\hat{V}_{CM2}$) determined at the fixed contact impedance 140 and zero bio-impedance 142 to determine the first and second compensation parameters ($A_0$ and $CMRR_{FD}$) of the second detection channel. To determine the first and second compensation parameters, the calibration device uses Equation (10). In particular, when the contact impedance is zero and the bio-impedance is fixed to an impedance value, Equation (10) may be represented as:

$$\hat{V}_{dm1}A_0 = \hat{V}_{dt1} + \hat{V}_{CM1}CMRR_{FD}.\qquad\text{Equation (11)}$$

When the contact impedance 140 is set to an impedance value and the bio-impedance is zero, Equation (10) may be represented as:

$$\hat{V}_{dm2}A_0 = \hat{V}_{dt2} + \hat{V}_{CM2}CMRR_{FD}.\qquad\text{Equation (12)}$$

Having two unknowns, Equations (11) and (12) may be solved together to obtain the first and second compensation parameters.

After setting the injection frequency at step 414, the calibration device determines the compensation parameter of the first detection channel. At step 424, the calibration device determines the first detection signal 144 (denoted herein as $\hat{V}_{INJ,t}$), for example using Equation (1). At step 426, the calibration device determines the first filtered signal 148 that is output by the first filter 120 and denoted herein as $\hat{V}_{INJ,m}$. At step 428, the calibration device determines the compensation parameter ($A_E$) of the first detection channel based on the first detection signal 144 and the first filtered signal 148. The calibration device may determine the compensation parameter ($A_E$) using Equation (5). In particular, the compensation parameter of the first detection channel may be determined as:

$$\hat{V}_{INJ,m}A_E = \hat{V}_{INJ,t}.\qquad\text{Equation (13)}$$

The calibration device, at step 430, causes the compensation parameter of the first detection channel and the first and second compensation parameters of the second detection channel to be stored in the measurement device 100. The procedure can be repeated for different frequencies. The measurement device 100 utilizes the compensation parameters as described herein to improve the obtained bio-impedance and contact impedance measurements.

Figure 5:
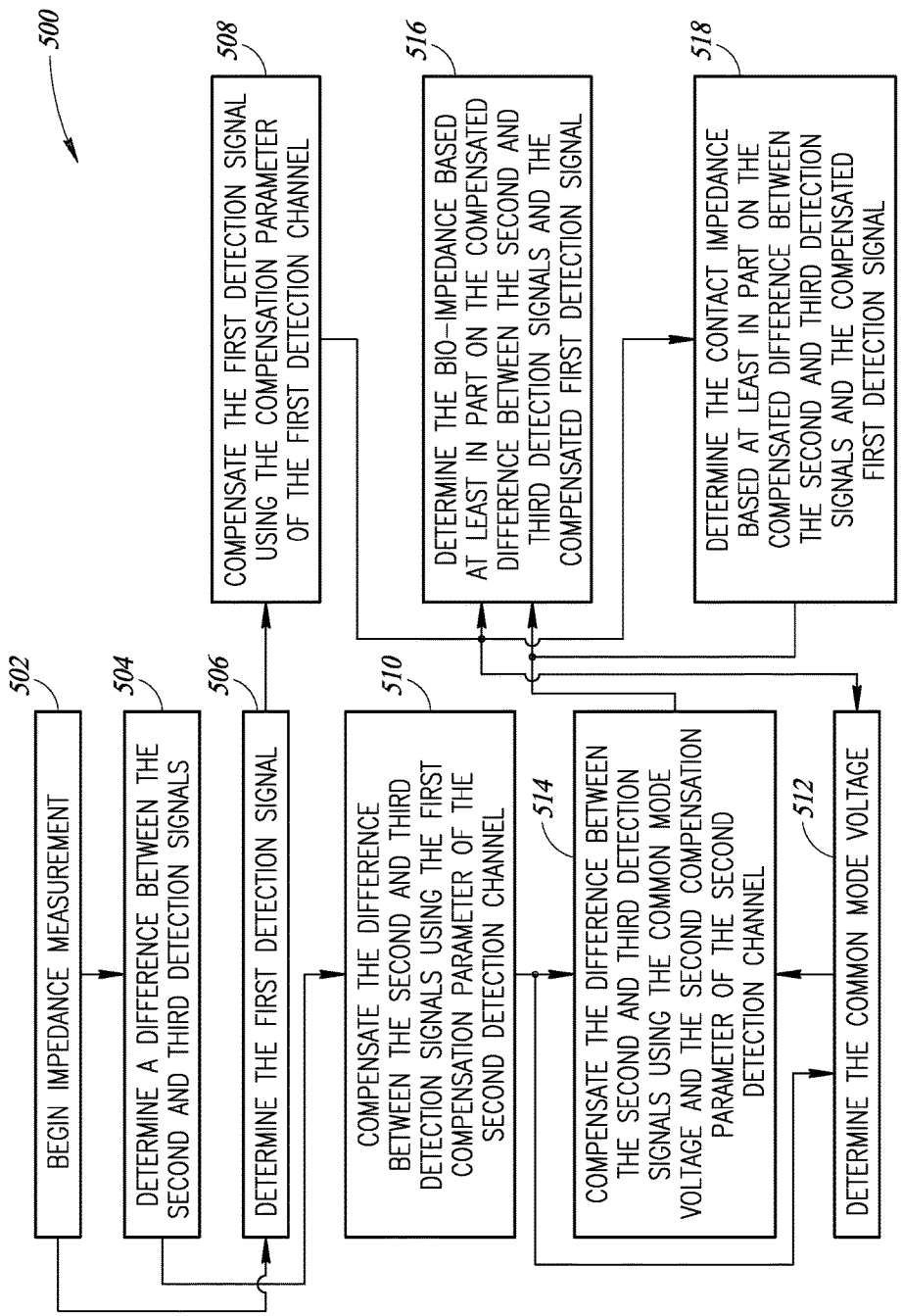
FIG. 5 shows a block diagram of a method for measuring impedance.

FIG. 5 shows a block diagram of a method 500 for measuring impedance. The method 500 may be performed by the measurement device 100. At step 502, the measurement device 100 begins an impedance measurement. To perform the impedance measurement, the measurement device 100 may be connected to a biological body 102 as described with reference to FIG. 1 herein, or through a different disposition of the 4 electrodes.

At step 504, the measurement device 100 determines a difference between the second and third detection signals 150, 152. The difference between the second and third detection signals 150, 152 is denoted herein as $\hat{V}_{dm}$. At step 506, the measurement device 100 determines the first detection signal 148 (denoted herein as $\hat{V}_{INJ,m}$).

At step 508, the measurement device 100 compensates the first detection signal using the compensation parameter of the first detection channel. To compensate the first detection signal, the measurement device 100 may scale the first detection signal by the compensation parameter of the first detection channel as:

$$\hat{V}_{INJ,C} = \hat{V}_{INJ,m}A_E.\qquad\text{Equation (14)}$$

At step 510, the measurement device 100 compensates the difference between the second and third detection signals using the first compensation parameter of the second detection channel. The measurement device 100 may compensate the difference between the second and third detection signals by scaling the difference by the first compensation parameter of the second detection channel as:

$$\hat{V}_{dC1} = \hat{V}_{dm}A_0.\qquad\text{Equation (15)}$$

At step 512, the measurement device 100 determines the common mode voltage. The common mode voltage (denoted as $\hat{V}_{CM}$) may be obtained from Equation (4c) assuming $V_{d,1} \approx V_d$. At step 514, the measurement device 100 compensates the difference between the second and third detection signals using the common mode voltage and the second compensation parameter of the second detection channel. The compensation performed at step 514 operates on the compensated difference performed at step 510. In an embodiment, the accuracy of the determination of the common mode voltage at step 512 may be improved through iteration of steps 512 and 514.

Compensating the difference between the second and third detection signals includes removing the contribution of common mode rejection from the difference between the second and third detection signals. The difference between the second and third detection signals may be compensated as:

$$\hat{V}_{dC2} = \hat{V}_{dC1} - CMRR_{FD}\hat{V}_{CM}.\qquad\text{Equation (16)}$$

The measurement device 100, at step 516, determines the bio-impedance based at least in part on the compensated difference between the second and third detection signals and the compensated first detection signal. This may be done using Equation (4a). The measurement device 100, at step 518, determines the contact impedance based at least in part on the compensated difference between the second and third detection signals and the compensated first detection signal. This may be done using Equation (4b).

In an embodiment, the waveform generator 134 may be an accumulator register and may be incremented by a fixed value each clock cycle. When the incremented sum, exceeds a maximum value that may be stored in the register, the incremented sum wraps around (for example, as a result of a modulo operation).

Figure 6:
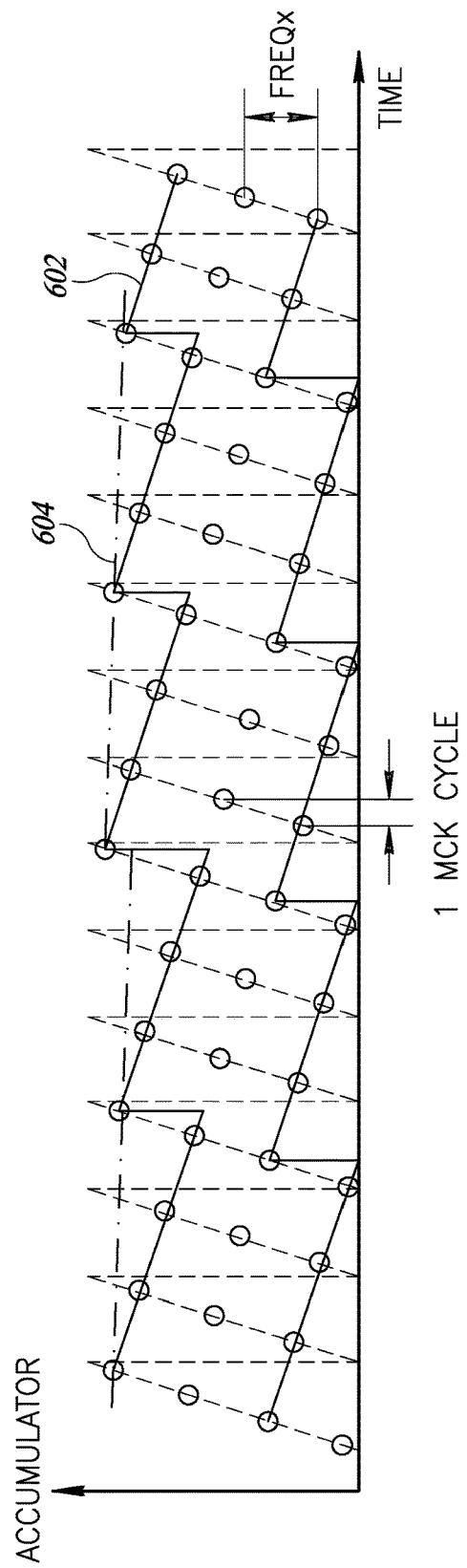
FIG. 6 shows an example of a waveform generated by an accumulator.

FIG. 6 shows an example of a waveform generated by an accumulator. The accumulator generates a sawtooth-like envelope for sine wave peaks and valleys that is in effect a sum of a sine wave and a sawtooth. Following an envelope "tooth," the accumulator output may be different from a previous cycle. Line 602 shows a first-order envelope of the accumulator output and line 604 shows a second-order envelope of the accumulator output.

The trigger signal 113 may follow the first-order envelope, the second-order envelope or an envelope of another order. If the frequency of all the resulting envelopes in the trigger signal 113 is large enough to be outside the acquisition signal bandwidth and filtered by the acquisition stage then the effect of the varying output of the accumulator is minimized. This may be taken into account before to set the frequency in the blocks 404, 414 (FIGS. 4A and 4B) and 502 (FIG. 5).

The frequency of the injected current may be significantly smaller than the clock frequency of the trigger signal 113. If the injected current frequency is not significantly smaller than the clock frequency of the trigger signal 113, the sample and hold trigger time quantization of the demodulators 118,124, 126 may not be negligible. Consequently, the detection signals 114, 150, 152 may not be sampled by the respective demodulators 118,124, 126 at a precise phase (for example, 0° and 90° for phase-quadrature demodulation). The resulting absolute time quantization error that affects the sampling triggers is modeled as delays (taken into account in $T_{D,I}$ and $T_{D,0}$) herein. The absolute time quantization errors are compensated by $A_E$ and $A_0$.

Further, another error (relative error) may be introduced between consecutive triggers of the trigger signal (for example, the time difference between a 0° trigger and a 90° trigger). Geometrically, the relative error may be modeled as a projection on two non-orthogonal axes (the ideal phase-quadrature demodulation is a projection of a sine wave on two orthogonal axes). The angle of deviation from orthogonality may be compensated in each detection signal 148 and 160. The compensation may be executed, immediately after the ADC conversion, in blocks 406, 416 and 426 (FIGS. 4A and 4B) and 504 and 506 (FIG. 5).

In low-power application, a slow clock frequency is used and granularity may be poor. Further, contrary to the absolute time quantization error, which results in a delay and which is taken into account in the formulas above, the relative error parameter may not be a delay or a gain error. The relative error parameter may be compensated during operation (also during calibration) after ADC conversion.

Figure 7:
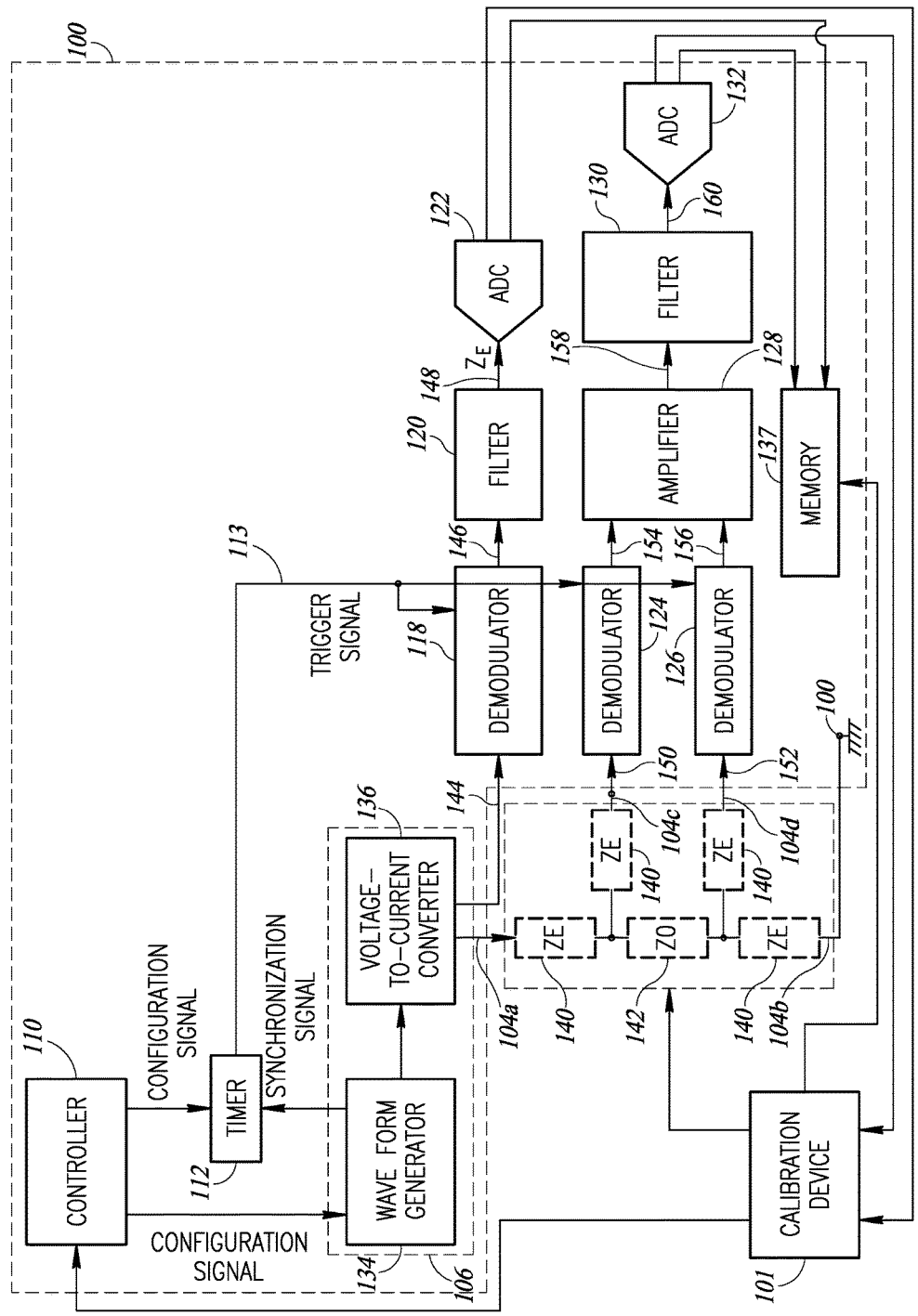
FIG. 7 shows a calibration device coupled to the measurement device.

FIG. 7 shows a calibration device 101 coupled to the measurement device 100. The calibration device 101 is used for determining the compensation parameters as described herein. The calibration device 101 is connected to the outputs of the ADCs 122, 132 and receives the converted signals from the ADCs 122, 132. The calibration device 101 is coupled to the controller 110, whereby the calibration device 101 may instruct the controller 110 to perform a frequency sweep for the injection current. The calibration device 101 is coupled to the memory 137.

The calibration device 101 may detect the converted filtered signals 148, 160 respectively output by the ADCs 122, 132. The calibration device 101 may use the detected signals to determine the compensation parameters as described herein.

The calibration device 101 may store the compensation parameters in the memory 137 of the measurement device 100. During use, the measurement device 100 may use the compensation parameters stored in the memory 137 to compensate for sources of error in the impedance measurements as described herein.

In an embodiment, the first detection channel 114 may be replicated. The detection channel replica may be configured to receive the third detection signal 152, for example, in the event that the two contact impedances 140 described with reference to FIG. 3 are different.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An impedance measurement device, comprising:
   memory configured to store a plurality of compensation parameters;
   first, second and third electrodes configured to be coupled to a biological body;
   a first detection channel configured to:
     receive a first detection signal detected by the first electrode, the first detection signal being representative of a bio-impedance of the biological body; and
     compensate the first detection signal using a first compensation parameter of the plurality of compensation parameters; and
   a second detection channel configured to:
     receive a second detection signal and a third detection signal detected by the second and third electrodes, respectively, the second and third detection signals being representative of the bio-impedance of the biological body;
     determine a difference between the second and third detection signals; and
     compensate the difference between the second and third detection signals using second and third compensation parameters of the plurality of compensation parameters and the compensated first detection signal;
   wherein the impedance measurement device generates a first output signal representative of a first impedance measurement and a second output signal representative of a second impedance measurement based on the compensated first detection signal and the compensated difference between the second and third detection signals, and determines a bio-impedance measurement indicative of a composition of the biological body based on the first and second output signals.

2. The impedance measurement device of claim 1, wherein the first and second detection channels are configured to compensate for a relative time quantization error introduced in a trigger signal used for sampling the first detection signal and the second and third detection signals.

3. The impedance measurement device of claim 1, wherein compensating the first detection signal using the first compensation parameter includes scaling an amplitude and adjusting a phase of the first detection signal by the first compensation parameter, wherein the first compensation parameter is a complex value.

4. The impedance measurement device of claim 1, wherein generating the first output signal includes:
   demodulating the compensated first detection signal to produce a first demodulated signal;
   filtering the first demodulated signal; and
   compensating the filtered first demodulated signal to produce the first output signal.

5. The impedance measurement device of claim 1, wherein compensating the difference between the second and third detection signals using the second and the third compensation parameters includes:
   compensating the difference between the second and third detection signals by the second compensation parameter;
   determining a common mode voltage based on the compensated difference between the second and third detection signals and the compensated first detection signal;
   compensating the common mode voltage by the third compensation parameter; and
   reducing the scaled difference between the second and the third detection signals by the scaled common mode voltage.

6. The impedance measurement device of claim 5, wherein generating the second output signal includes:
   demodulating the second and third detection signals;
   amplifying the difference between the second and third detection signals to produce an amplified signal;
   filtering the amplified signal; and
   compensating the filtered amplified signal to produce the second output signal.

7. The impedance measurement device of claim 1, wherein the first detection channel includes a first demodulator and the first compensation parameter compensates for a gain of the first demodulator and an absolute time quantization error of the first demodulator.

8. The impedance measurement device of claim 1, wherein the second detection channel includes a second demodulator, a third demodulator and an amplifier and the second compensation parameter compensates for a gain of the second demodulator or the third demodulator and an absolute time quantization error of the second demodulator or the third demodulator and a gain of the amplifier.

9. The impedance measurement device of claim 8, wherein the second detection channel is configured to use the third compensation parameter to compensate for a common mode rejection ratio of the second demodulator and the third demodulator.

10. A method of measuring impedance, the method comprising:
    detecting a first, second and third detection signals by a first, second and third electrodes, respectively, that are coupled to a biological body;
    using a first detection channel, receiving the first detection signal representative of a bio-impedance of the biological body;
    using the first detection channel, compensating the first detection signal using a first compensation parameter of a plurality of compensation parameters;
    using a second detection channel, receiving the second detection signal and the third detection signal, the second and third detection signals being representative of the bio-impedance of the biological body;
    determining a difference between the second and third detection signals;
    using the second detection channel, compensating the difference between the second and third detection signals using second and third compensation parameters of the plurality of compensation parameters and the compensated first detection signal;
    generating a first output signal representative of a first impedance measurement and a second output signal representative of a second impedance measurement based on the compensated first detection signal and the compensated difference between the second and third detection signals; and
    determining a bio-impedance measurement indicative of a composition of the biological body based on the first and second output signals.

11. The method of claim 10, comprising:
    compensating the first, second and third detection signals for a relative time quantization error introduced in a trigger signal used for sampling the first detection signal and the second and third detection signals.

12. The method of claim 10, wherein compensating the first detection signal using the first compensation parameter includes scaling an amplitude and adjusting a phase of the first detection signal by the first compensation parameter, wherein the first compensation parameter is a complex value.

13. The method of claim 10, wherein generating the first output signal includes:
    demodulating the first detection signal to produce a first demodulated signal;
    filtering the first demodulated signal; and
    compensating the filtered first demodulated signal to produce the first output signal.

14. The method of claim 10, wherein compensating the difference between the second and the third detection signals using the second and the third compensation parameters includes:
    compensating the difference between the second and third detection signals by the second compensation parameter;
    determining a common mode voltage based on the compensated difference between the second and third detection signals and the compensated first detection signal;
    compensating the common mode voltage by the third compensation parameter; and
    reducing the scaled difference between the second and third detection signals by the scaled common mode voltage.

15. The method of claim 14, wherein generating the second output signal includes:
    demodulating the second and third detection signals;
    amplifying the difference between the second and third detection signals to produce an amplified signal;
    filtering the amplified signal; and
    compensating the filtered amplified signal to produce the second output signal.

16. The method of claim 10, wherein the first detection channel includes a first demodulator and the first compensation parameter compensates for a gain of the first demodulator and an absolute time quantization error of the first demodulator.

17. An impedance measurement device, comprising:
a plurality of electrodes configured to be coupled to a biological body, the plurality of electrodes including a first, second and third electrodes;
a current generator configured to supply current to the plurality of electrodes;
memory configured to store a plurality of compensation parameters; and
a voltage detector including:
  a first detection channel configured to:
    receive a first detection signal detected by the first electrode and representative of a bio-impedance of the biological body; and
    compensate the first detection signal using a first compensation parameter of the plurality of compensation parameters, and
  a second detection channel configured to:
    receive second and third detection signals detected by the second and third electrodes, respectively, and representative of the bio-impedance of the biological body;
    determine a difference between the second and third detection signals; and
    compensate the difference between the second and third detection signals using second and third compensation parameters of the plurality of compensation parameters and the compensated first detection signal,
wherein the impedance measurement device generates a first output signal representative of a first impedance measurement and a second output signal representative of a second impedance measurement based on the compensated first detection signal and the compensated difference between the second and third detection signals, and determines a bio-impedance measurement indicative of a composition of the biological body based on the first and second output signals.

18. The impedance measurement device of claim 17, wherein the impedance measurement device is part of a watch, activity tracker, chest band or patch.

19. The impedance measurement device of claim 17, wherein the first and second detection channels are configured to compensate for a relative time quantization error introduced in a trigger signal used for sampling the first detection signal and the second and third detection signals.

20. The impedance measurement device of claim 17, wherein compensating the first detection signal using the first compensation parameter includes scaling an amplitude and adjusting a phase of the first detection signal by the first compensation parameter, wherein the first compensation parameter is a complex value.

* * * * *